United States Patent [19]

Pera et al.

[11] Patent Number: 4,920,107
[45] Date of Patent: Apr. 24, 1990

[54] 1-METHYL-3,5,7-TRIAZA-1-AZONIATRICYCLODECANE COMPOUNDS, A METHOD FOR PREPARING THESE COMPOUNDS, AND THEIR USE IN THE CONTROL OF MICROORGANISMS IN AQUEOUS SYSTEMS

[75] Inventors: John D. Pera, Cordova; S. Rao Rayudu, Germantown, both of Tenn.

[73] Assignee: Buckman Laboratories International, Inc., Memphis, Tenn.

[21] Appl. No.: 174,812

[22] Filed: Mar. 29, 1988

[51] Int. Cl.$^5$ ............... C07D 487/18; A01N 43/90; C10M 105/58; C09D 5/14
[52] U.S. Cl. ............... 514/244; 544/185; 544/186; 422/16; 422/1; 422/17; 252/34; 252/49.3; 252/49.5; 252/401; 252/402; 106/18.29; 106/18.32; 106/18.33
[58] Field of Search ............... 544/185, 186; 422/1, 422/16, 17; 252/34, 401, 49.3, 49.5; 514/244; 106/18.29, 18.32, 18.33

[56] References Cited

U.S. PATENT DOCUMENTS

| | | | |
|---|---|---|---|
| Re. 29,226 | 5/1977 | Paul et al. | 544/185 |
| 3,624,253 | 11/1971 | Pawloski | 544/185 |
| 3,908,009 | 9/1975 | Polemenakos et al. | 544/185 |
| 4,505,831 | 3/1985 | Fenyes et al. | 252/34 |
| 4,650,866 | 3/1987 | Rayudu | 544/186 |

OTHER PUBLICATIONS

Friedrich et al., Zur Kenntnis des Hexamethylenetetramines I., 54B Berichte 1531–42, (1921), (Including English Language Abstract).

*Primary Examiner*—John M. Ford
*Attorney, Agent, or Firm*—Finnegan, Henderson, Farabow, Garrett & Dunner

[57] ABSTRACT

A method of preserving an aqueous system which is susceptible to microbiological degradation, comprising the step of adding to the system a compound having the formula

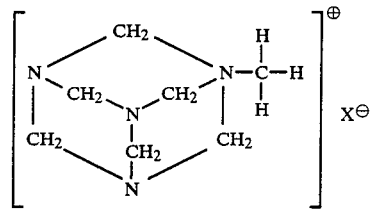

wherein X is an anion selected from the group consisting of sulfate, acetate and citrate groups, and wherein the compound is added in an amount sufficient to inhibit the growth and proleferation of at least one microogranism in the aqueous system.

The compounds 1-methyl-3,5,7-triaza-1-azoniatricyclodecane acetate and 1-methyl-3,5,7-triaza-1-azoniatricyclodecane citrate, and a method for preparing these compounds comprising the reaction of ammonium citrate, or ammonium acetate, with methylamine, formaldehyde and ammonia in an aqueous medium.

25 Claims, No Drawings

1-METHYL-3,5,7-TRIAZA-1-AZONIATRICYCLO-DECANE COMPOUNDS, A METHOD FOR PREPARING THESE COMPOUNDS, AND THEIR USE IN THE CONTROL OF MICROORGANISMS IN AQUEOUS SYSTEMS

FIELD OF THE INVENTION

The present invention relates to a method for the preservation of aqueous systems which are susceptible to microbiological degradation through the use of certain 1-methyl-3,5,7-triaza-1-azoniatricyclodecane compounds. Typical systems include aqueous solutions, emulsions and suspensions.

The present invention also relates to the novel compounds 1-methyl-3,5,7-triaza-1-azoniatricyclodecane acetate and 1-methyl-3,5,7-triaza-1-azoniatricyclodecane citrate, and a method for their preparation.

BACKGROUND OF THE INVENTION

A large number of commercial and industrial products comprise aqueous systems containing organic materials. Examples are latexes, surfactants, dispersants, stabilizers, thickeners, adhesives, starches, waxes, proteins, emulsifying agents, detergents, cellulose products, and resins formulated in aqueous solutions, emulsions or suspensions. Such products frequently contain relatively large amounts of water. The temperature at which these products are stored, as well as their pH, makes these products susceptible to the growth of microorganisms. These microorganisms can be introduced during the manufacturing of these products (from exposure to air, tanks, pipes, equipment, and humans), and/or during their use (from multiple openings and reclosures of packaged products, and introduction of contaminated objects to stir or remove material).

Microbiological degradation of aqueous systems containing organic material may manifest itself in a variety of problems. These include loss of viscosity, gas formation, objectionable odors, decreased pH, emulsion breaking, color change, and gelling.

Friedrich et al., *Zur Kenntnis des Hexamethylentetramins, I.*, 54B Berichte 1531-42 (1921), discloses 1-methyl-3,5,7-triaza-1-azoniatricyclodecane compounds which include anions such as methyl sulfate, nitrate, picrate, perchlorate, and thiocyanate groups.

U.S. Pat. Nos. 4,505,831 and 4,650,866 disclose 1-methyl-3,5,7-triaza-1-azoniatricyclodecane compounds, useful as microbicides. These patents, however, are limited to such compounds having halide anions. U.S. Pat. No. 4,650,866 also discloses a method for preparing such 1-methyl-3,5,7-triaza-1-azoniatricyclodecane halides comprising the reaction of an ammonium halide with methylamine, formaldehyde and ammonia in an aqueous medium.

DESCRIPTION OF THE INVENTION

The present invention provides a method for the preservation of an aqueous system which is susceptible to microbiological degradation, comprising the step of adding to the system a compound having the formula

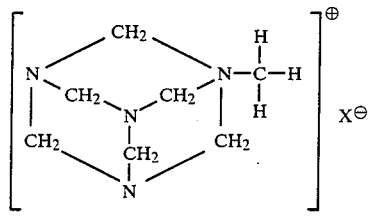

wherein X is an anion selected from the group consisting of sulfate, acetate and citrate groups, and wherein the compound is added in an amount sufficient to inhibit the growth and proliferation of at least one microorganism in the aqueous system.

The sulfate anions of the compounds of the invention include, for example, methyl sulfate. Compounds of the invention having sulfate groups as the anion may be prepared by methods known in the art, such as the method disclosed in Friedrich et al., above.

The present invention also provides a method for preparing compounds of the invention comprising the reaction of an ammonium compound with methylamine, formaldehyde and ammonia in an aqueous medium. Ammonium acetate may be used in this process as the ammonium compound in the preparation of 1-methyl-3,5,7-triaza-1-azoniatricyclodecane acetate, while ammonium citrate may be used as the ammonium compound in the preparation of 1-methyl-3,5,7-triaza-1-azoniatricyclodecane citrate. This process is an economical method for making the compounds of the instant invention. All of the starting materials for this process are readily available commercial products.

In the method of preparation of the present invention, each mole of ammonium compound is preferably reacted with about 0.75 to 2 moles of methylamine as a source of an N-methyl group, 5.75 to 12 moles of formaldehyde, and 1.75, more preferably 2, or more moles, of ammonia. Most preferably, from 2 to 4 moles of ammonia per mole of ammonium compound are used in this reaction.

The process of preparation is preferably conducted at a temperature of from about 40° to 70° C. More preferably, the process is conducted in the range of about 45° to 50° C.

The process is preferably run by forming an aqueous reaction medium by treating formaldehyde with a mixture of ammonium compound and methylamine while keeping the temperature around about 45° C. Ammonia is then preferably added to the reaction medium, the temperature of which is preferably kept below 50° C. The amount of ammonia added is preferably 1.75, more preferably 2, or more moles per mole of ammonium compound to bring the pH of the final reaction medium, preferably an aqueous solution, within the range of from about 6 to 8.

The reaction is conducted for a time sufficient to prepare the quaternary ammonium salts of the present invention. Preferably, the reaction is conducted for about 2 hours to 6 hours, more preferably for about 2 hours.

The method of this invention may be used to prevent microbiological degradation in any aqueous system susceptible to such degradation, such as aqueous solutions, emulsions and suspensions.

Examples of aqueous solutions, emulsions, and suspensions which are subject to microbiological degradation include water-based paints, latex emulsions, such as acrylic and polyvinyl acetate emulsions, adhesive solutions and emulsions, wax emulsions, polishes, metalworking fluid solutions and emulsions, caulking and sealant products, papermaking chemical products such as alum solutions, clay and pigment dispersions, starch slurries and solutions, and protein coating formulations, and cosmetic preparations. Many of these materials are also used in other industrial and commercial products. Aqueous systems may be used in petroleum production and in the manufacture of detergents, surfactants, inks and textiles.

A particularly preferred use of the compounds of the present invention is in the preservation of water-based paints or cutting fluids, such as cutting oil solutions or emulsions.

The antimicrobial activity of the compounds used in accordance with the invention extends to a variety of different microorganisms, including bacteria such as *Escherichia coli, Staphylococcus aureus, Pseudomonas aeruqinosa, Enterobacter aeroqenes, Klebsiella pneumoniae, Proteus vulqaris, Salmonella choleraesuis* and *Bacillus subtilis*, and fungi such as *Candida albicans* and *Aspergillus niger*.

The concentration of the compounds of this invention which inhibits growth and proliferation of a microorganism, and thus provides the preservative effect described herein, may be readily determined by one skilled in the art without extensive experimentation and, preferably, will range from about 25 parts to about 5000 parts by weight of the compound for one million parts of the aqueous system to be preserved.

This invention also relates to the novel compounds 1-methyl-3,5,7-triaza-1-azoniatricyclodecane acetate and 1-methyl-3,5,7-triaza-1-azoniatricyclodecane citrate. These novel compounds are especially preferred for prevention of microbiological degradation in aqueous systems.

The compounds of the invention may be utilized as solids or may be dissolved in water prior to addition to the product being preserved. In those instances wherein the presence of water might cause some degradation of the quaternary ammonium salts over a long period of time, non-aqueous dispersions could be prepared by the proper selection of solvents, dispersants, and stabilizers which are well-known in the art as being suitable for the formation of such dispersions.

In those instances wherein the compounds of the invention are subject to rapid degradation by heat, stabilizers may be added.

To illustrate the nature of the invention, the following examples are given. It should be understood, however, that the invention is not to be limited to the specific conditions or details set forth in these examples.

EXAMPLE 1

Preparation of
1-Methyl-3,5,7-triaza-1-azoniatricyclodecane acetate

A 500 ml, three-neck flask equipped with a reflux condenser, a mechanical stirrer, a thermometer and a dropping funnel, was charged with 38.5 g (0.5 mole) of ammonium acetate, and 31.0 g (0.5 mole) of 50% aqueous methylamine. To the above well-agitated mixture were slowly added 243.3 g (3.0 mole) of 37% aqueous formaldehyde, while maintaining the temperature between 45° and 50° C. After completing this addition and while continuing vigorous agitation, 58.6 g (1.0 mole) of 29% aqueous ammonia were introduced at such a rate as to maintain the temperature between 45° and 50° C. Stirring was continued for an additional 2 hours while the temperature fell gradually to the ambient. The resulting water-clear solution was analysed by HPLC. This solution contained 26.6% (80% yield) by weight of the 1-methyl-3,5,7-triaza-1-azoniatricyclodecane acetate.

EXAMPLE 2

Preparation of
1-Methyl-3,5,7-triaza-1-azoniatricyclodecane citrate

A 500 ml, three-neck flask equipped with a reflux condenser, a mechanical stirrer, a thermometer and a dropping funnel was charged with 56.5 g (0.25 mole) of ammonium citrate and 31.0 g (0.5 mole) of 50% aqueous methylamine. To the above well-agitated mixture were slowly added 243.3 g (3.0 mole) of 37% aqueous formaldehyde, while maintaining the temperature between 45° and 50° C. After completing this addition and while continuing vigorous agitation, 58.6 g (1.0 mole) of 29% aqueous ammonia were introduced at such a rate as to maintain the temperature between 45° and 50° C. Stirring was continued for an additional two hours while the temperature fell gradually to the ambient. The resulting water-clear solution was analyzed by HPLC. The solution contained 22.43% (72% yield) by weight of the 1-methyl-3,5,7-triaza-1-azoniatricyclodecane citrate.

EXAMPLE 3

The preservative effectiveness of the quaternary ammonium salts prepared in Examples 1 and 2 was determined in a freshly prepared water-based paint formulated with titanium dioxide and calcium carbonate as pigments, an acrylic emulsion resin, dispersants, and hydroxyethyl cellulose as thickener. The pH of this paint was approximately 9.0. The procedure used was as follows:

A. Weigh 100 g. of paint into prenumbered French square bottles.

B. Add the appropriate amount of the preservative to obtain the desired parts per million.

C. Add 1 ml. of inoculum. Mix well by shaking the contents of each bottle immediately after the addition of the inoculum. The inoculum was prepared by adding 2 ml. of sterile saline solution to an 18- to 24-hr. agar culture of *Enterobacter aeroqenes*, agitating to loosen the surface growth, and decanting to a sterile test tube. The procedure was repeated with cultures of *Pseudomonas aeruqinosa* and *Bacillus subtilis*, and all three suspensions were decanted to the same test tube. The concentration of the mixed bacterial suspension was then adjusted so that a final concentration of $1 \times 10^5$ cells per ml. is achieved when one ml. of the inoculum is added to 100 ml. of the paint.

D. Include a minimum of two controls (bottles containing substrate and inoculum only).

E. Incubate at 37° C. for 9 weeks.

F. Streak from the contents of each bottle onto nutrient agar plates at intervals of 1 day, 2 days, 3 days, 7 days, and 21 days after each challenge. Incubate the streaked plates at 37° C. for 24 hours.

G. Reinoculate the test with the same test organisms at the end of 21 days and again at the end of 42 days.

H. Observe the streaked plates for growth after 24 hours of incubation.

I. Observe the contents of each bottle for

1. Color change
2. Odor
3. Thickening of paint

J. Evaluate the results. A chemical is considered an effective preservative when it prevents the growth of bacteria 21 days after each inoculation.

The quaternary ammonium compounds described in Examples 1 and 2 were effective preservatives at concentrations of 200 parts of the salt per one million parts of paint and higher concentrations. No color changes were noted in any of the tests. In addition, no undesirable odors were observed and the viscosities of the preserved paint samples did not change.

EXAMPLE 4

The antimicrobial effectiveness of 1-methyl-3,5,7-triaza-1-azoniatricyclodecane acetate and 1-methyl-3,5,7-triaza-1-azoniatricyclodecane citrate was determined by the method for the preservation of an organic substance described in the United States Pharmacopeia, 21st revision (Jan. 1, 1985), "Microbiological Test #51" p. 1151. Test results are given in Table 1.

TABLE 1

| MINIMUM INHIBITORY CONCENTRATION (ppm) vs. | | | | | |
|---|---|---|---|---|---|
| COMPOUND | E. coli | S. aureus | P. aeruginosa | C. albicans | A. niger |
| 1-methyl-3,5,7-triaza-1-azoniatricyclodecane acetate | 500 | 500 | 300 | 500 | 200 |
| 1-methyl-3,5,7-triaza-1-azoniatricyclodecane citrate | 500 | 300 | 500 | 500 | 500 |

EXAMPLE 5

The compounds of the present invention are also effective in preserving synthetic, soluble, and semi-synthetic metalworking fluids. The tests were conducted following ASTM's Evaluation of Antimicrobial Agents in Aqueous Metalworking Fluids (designation E686-80).

The quaternary ammonium compounds described in Examples 1 and 2 preserve the soluble-oil metalworking fluids against bacterial attack at 300 parts, the semi-synthetic oils at 200 parts, and the synthetic oils at 200 parts of these compounds per one million parts of the metalworking fluids.

We claim:

1. A method of preserving an aqueous system which is susceptible to microbiological degradation, comprising the step of adding to said system a compound having the formula wherein X is an anion selected from the group consisting of sulfate, acetate and citrate groups, and wherein said compound is added in an amount sufficient to inhibit the growth and proliferation of at least one microorganism in said aqueous system.

2. The method of claim 1, wherein said aqueous system is selected from the group consisting of aqueous solutions, emulsions and suspensions.

3. The method of claim 2, wherein said aqueous system is a water-based paint.

4. The method of claim 2, wherein said aqueous system is a cutting fluid.

5. The method of claim 1, wherein said compound is 1-methyl-3,5,7-triaza-1-azoniatricyclodecane acetate.

6. The method of claim 5, wherein said aqueous system is a water-based paint.

7. The method of claim 5, wherein said aqueous system is a cutting fluid.

8. The method of claim 1, wherein said compound is 1-methyl-3,5,7-triaza-1-azoniatricyclodecane citrate.

9. The method of claim 8, wherein said aqueous system is a water-based paint.

10. The method of claim 8, wherein said aqueous system is a cutting fluid.

11. The method of claim 1, wherein said compound is 1-methyl-3,5,7-triaza-1-azoniatricyclodecane methyl sulfate.

12. The method of claim 11, wherein said aqueous system is a water-based paint.

13. The method of claim 11, wherein said aqueous system is a cutting fluid.

14. The compound 1-methyl-3,5,7-triaza-1-azoniatricyclodecane acetate.

15. A method of making 1-methyl-3,5,7-triaza-1-azoniatricyclodecane acetate comprising the step of reacting ammonium acetate with methylamine, formaldehyde and ammonia in an aqueous medium for a time sufficient to obtain said 1-methyl-3,5,7-triaza-1-azoniatricyclodecane acetate.

16. The compound 1-methyl-3,5,7-triaza-1-azoniatricyclodecane acetate made by the process of claim 15.

17. The compound 1-methyl-3,5,7-triaza-1-azoniatricyclodecane citrate.

18. A method of making 1-methyl-3,5,7-triaza-1-azoniatricyclodecane citrate comprising the step of reacting ammonium citrate with methylamine, formaldehyde and ammonia in an aqueous medium for a time sufficient to obtain said 1-methyl-3,5,7-triaza-1-azoniatricyclodecane citrate.

19. The compound 1-methyl-3,5,7-triaza-1-azoniatricyclodecane citrate made by the process of claim 18.

20. The method of claim 1 wherein said compound is added in the amount of from about 25 parts to about 5000 parts by weight for each one million parts by weight of the aqueous system to be preserved.

21. A process of preparing a compound of the formula wherein X is an anion selected from the group consisting of sulfate, acetate and citrate groups, which comprises the step of reacting an ammonium compound selected from the group consisting of ammonium acetate and ammonium citrate with methyl amine, formaldehyde and ammonia in an aqueous medium for a time sufficient to prepare said compound.

22. The process of claim 21 wherein each mole of said ammonium compound is reacted with 0.75 to 1.25 moles of methyl amine, 5.75 to 12 moles of formaldehyde and 1.75 or more moles of ammonia.

23. The process of claim 21, wherein each mole of said ammonium compound is reacted with 2 to 4 moles of ammonia.

24. The process of claim 21, wherein the temperature is maintained at about 40° to 70° C.

25. The process of claim 21, wherein the reaction is conducted for from about two to six hours.

* * * * *